United States Patent [19]

Silvis et al.

[11] Patent Number: 4,605,789

[45] Date of Patent: Aug. 12, 1986

[54] PROCESS FOR PREPARING SPIROBIINDANOLS

[75] Inventors: H. Craig Silvis; Ted A. Morgan, both of Midland, Mich.

[73] Assignee: The Dow Chemical Company, Midland, Mich.

[21] Appl. No.: 812,616

[22] Filed: Dec. 23, 1985

[51] Int. Cl.$^4$ .............................................. C07C 39/17
[52] U.S. Cl. .................................. 568/721; 568/719; 568/744; 568/806
[58] Field of Search ................ 568/744, 721, 719, 806

[56] References Cited

U.S. PATENT DOCUMENTS 2,176,882 10/1955 Fisher .................................. 568/719
3,419,624 12/1968 Cotler et al. ........................ 568/719
4,334,106 6/1982 Dae ..................................... 568/721

Primary Examiner—Werren B. Lone

[57] ABSTRACT

A new process for preparing spirobiindanols, comprising refluxing the corresponding alkylaryl bisphenyl derivative in the presence of a dry heterogeneous acid catalyst in toluene, is disclosed.

4 Claims, No Drawings

PROCESS FOR PREPARING SPIROBIINDANOLS

BACKGROUND OF THE INVENTION

This invention relates to a novel process for preparing spirobiindanols. The process employs an alkylaryl bisphenol in the presence of a dry heterogeneous acid catalyst in toluene at reflux.

The use of mineral acids, such as 18 percent aqueous HBr, concentrated aqueous $H_2SO_4$ (U.S. Pat. No. 3,271,463), Lewis acids such as $BF_3$, and p-toluenesulfonic acid as catalysts for the conversion of bisphenols to spirobiindanols is well known. These procedures, however, require costly catalyst removal steps, such as washing and neutralization, in the purification of the final product because the catalyst is dissolved in the reaction mixture or is present in a second phase. Furthermore, the crude products obtained by these methods are very difficult to purify due to the presence of many by-products. Spirobiindanols are also available from phenol and acetone via the bisphenol derivative.

The process of the present invention provides a cleaner crude product under milder conditions with an easier and less costly catalyst removal step. The catalyst allows for faster conversion and can also be easily recycled. In summary, the advantages of this process over the known methods are: (1) the reaction is faster; (2) the reaction conditions are milder as far as temperature and corrosiveness; (3) the catalyst can be removed more easily; (4) the catalyst can be easily recycled; (5) higher yields; and (6) the crude product is cleaner and more easily purified.

Spirobiindanols impart high rigidity, lipophilicity, and oxidative and thermal stability to polymer systems such as epoxies, polyesters, and polycarbonates. Spirobiindanols are also applicable in membranes for gas separation. Spirobiindanols can also be reacted with halohydrins to form diglycidyl ethers and diglycidyl ethers to form polyhydroxy ethers which are useful in thermoforming processes, for the manufacture of articles such as combs and high temperature structural parts, and for use as adhesives.

SUMMARY OF THE INVENTION

This invention relates to a novel process for the preparation of spirobiindanols. The process employs alkylaryl bisphenols in the presence of a dry heterogeneous acid catalyst in toluene under reflux. Specifically, this invention relates to a process for preparing spirobiindanols which comprises refluxing the corresponding alkylaryl bisphenol derivative in the presence of a dry heterogeneous acid catalyst in an aromatic hydrocarbon solvent; wherein said spirobiindanols have the general formula:

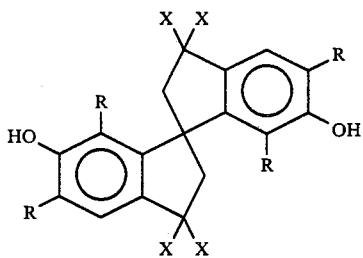

wherein R is selected from the group consisting of hydrogen, hydrocarbon radicals, halogen radicals and mixtures thereof. The X radical may be any linear alkyl hydrocarbon radical with a carbon chain length of 1 to 4. So far as is known at this time, the X radicals need not be identical for the purpose of this invention. It is preferred, however, that X be the methyl radical.

DETAILED DESCRIPTION OF THE INVENTION

The bisphenols employed to obtain the spirobiindanols of the present invention have the general formula:

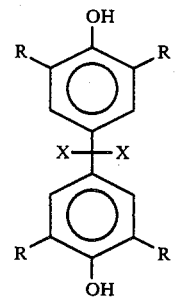

wherein R is selected from the group consisting of hydrogen, hydrocarbon radicals, halogen radicals and mixtures thereof, and X is any linear alkyl hydrocarbon radical with a chain length of 1 to 4 carbon atoms. So far as is known at this time, X may be asymmetrical. It is optimal that X be a methyl radical.

Examples of suitable bisphenols include:

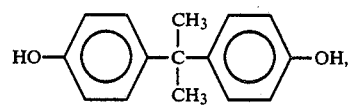

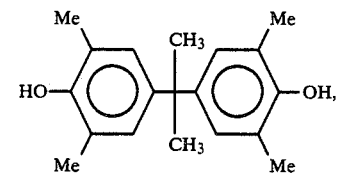

and mixtures thereof.

Examples of suitable hydrocarbon radicals for R for the spirobiindanol and the bisphenol include alkyl radicals such as methyl, ethyl, isopropyl and butyl radicals; alkenyl radicals such as vinyl and allyl radicals; alkynyl radicals such as acetylene and propyne radicals; aryl radicals such as phenyl, naphthyl, and biphenyl radicals; and corresponding substituted hydrocarbon radicals such as nitromethyl radicals. It is preferred that the hydrocarbon radical be an alkyl radical, with the methyl radical being optimal. Examples of suitable halogen radicals include bromine and chlorine radicals.

So far as is known at this time, any dry heterogeneous acidic ion exchange resin can act as the catalyst in this process. It is preferred, however, that the resin be a strong acid cation exchange resin. It is optimal that it be composed of sulfonated styrene-divinylbenzene copolymer in bead form with an acid equivalent weight of the dry resin being about 222 g.

So far as is known, any aromatic hydrocarbon solvent can be employed for the purposes of the present invention. The solvent must have the capacity to swell the ion exchange resin beads to expose acid sites, as well as dissolve the bisphenol substrate. Examples of suitable solvents include benzene, cyclohexanone, butyl acetate, methylene chloride, toluene and xylene. It is preferred, however, that the solvent be toluene.

Now in order that those skilled in the art may better understand how the present invention can be practiced, the following example is given by way of illustration and not by way of limitation.

EXAMPLE

To a 1-liter round-bottom flask equipped with a reflux condenser, magnetic stir bar, and thermowell, the following were heated to a reflux temperature of 113° C. with stirring: 56.8 g (0.2 moles) of tetramethylbisphenol A, 28 grams of Dowex* MSC-1 H (a strong acid cation exchange resin composed of sulfonated styrene-divinylbenzene copolymer in bead form with an acid equivalent weight of about 222 g; manufactured by The Dow Chemical Company), which was dried at 120° C. at 1 mm Hg for 16 hours, and 400 ml of toluene. After 6 hours of reflux, the hot reaction mixture was suction-filtered through a sintered-glass funnel to remove the catalyst. Before cooling the filtration slowly to 25° C., 400 ml of hexane was added. The resultant off-white crystalline solid (16.5 g; 67 percent yield) was collected by suction filtration. This material was recrystallized from a hot 1:1 hexane/toluene mixture to give a white crystalline solid, which had a melting point range of 190.5° to 191.5° C. The resulting spirobiindanol had the general formula:

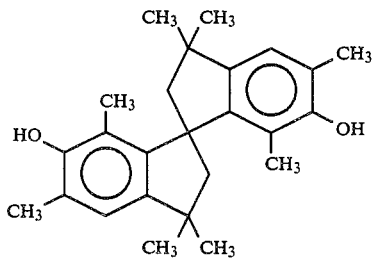

*Trademark of The Dow Chemical Company.

What is claimed is:

1. A process for making spirobiindanols which comprises refluxing the corresponding alkylaryl bisphenol derivative, having the general formula

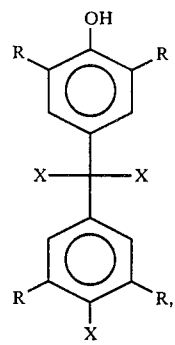

in the presence of a dry heterogeneous acidic ion exchange resin as the catalyst in an aromatic hydrocarbon solvent, wherein said spirobiindanols have the general formula

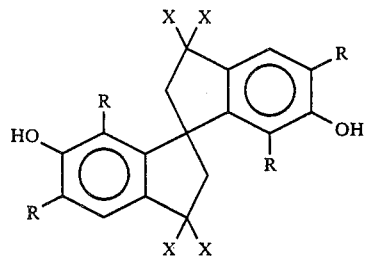

wherein R is selected from the group consisting of hydrogen, hydrocarbon radicals, halogen radicals and mixtures thereof, and X is a linear alkyl hydrocarbon radical with a carbon chain length of 1 to 4.

2. The process as defined in claim 1 wherein R is a hydrocarbon radical, X is a methyl radical, the catalyst is a strong acid cation exchange resin, and the aromatic solvent is toluene.

3. The process as defined in claim 2 wherein R is an alkyl radical and the catalyst is composed of sulfonated styrene-divinylbenzene copolymer in bead form with an acid equivalent weight of about 222 g.

4. The process as defined in claim 3 wherein R is the methyl radical.

* * * * *